(12) United States Patent
Kassab

(10) Patent No.: US 8,361,101 B2
(45) Date of Patent: Jan. 29, 2013

(54) DEVICES, SYSTEMS AND METHODS FOR CONTROLLING LOCAL BLOOD PRESSURE

(75) Inventor: Ghassan S. Kassab, Zionsville, IN (US)

(73) Assignee: DTherapeutics, LLC, Zionsville, IN (US)

( * ) Notice: Subject to any disclaimer, the term of this patent is extended or adjusted under 35 U.S.C. 154(b) by 1170 days.

(21) Appl. No.: 11/720,224

(22) PCT Filed: Nov. 28, 2005

(86) PCT No.: PCT/US2005/042911
§ 371 (c)(1),
(2), (4) Date: May 25, 2007

(87) PCT Pub. No.: WO2006/058289
PCT Pub. Date: Jun. 1, 2006

(65) Prior Publication Data
US 2008/0195138 A1    Aug. 14, 2008

Related U.S. Application Data

(60) Provisional application No. 60/630,563, filed on Nov. 26, 2004.

(51) Int. Cl.
*A61M 29/00* (2006.01)

(52) U.S. Cl. ...................................................... 606/198

(58) Field of Classification Search .................. 606/191, 606/192, 194, 198; 623/1.11, 1.12
See application file for complete search history.

(56) References Cited

U.S. PATENT DOCUMENTS

| 5,244,460 | A | * | 9/1993 | Unger et al. | 604/508 |
|---|---|---|---|---|---|
| 6,632,196 | B1 | | 10/2003 | Houser | |
| 7,303,571 | B2 | * | 12/2007 | Makower et al. | 606/158 |
| 2002/0082636 | A1 | * | 6/2002 | Sawhney et al. | 606/193 |
| 2004/0098030 | A1 | * | 5/2004 | Makower et al. | 606/200 |
| 2004/0098118 | A1 | | 5/2004 | Granada | |

OTHER PUBLICATIONS

International Searching Authority, International Search Report, mailed May 19, 2008 (PCT/US05/42911).
International Searching Authority, International Written Opinion, mailed May 19, 2008 (PCT/US05/42911).

* cited by examiner

*Primary Examiner* — Ryan Severson
*Assistant Examiner* — Jonathan W Miles
(74) *Attorney, Agent, or Firm* — Ice Miller LLP

(57) ABSTRACT

The present invention discloses devices, systems and methods for increasing blood pressure in a blood vessel by introducing an anchor within that traps a particle capable of increasing in volume as it is exposed to blood flow. As the particle increases in volume, it serves to decrease the cross sectional area of the blood vessel, resulting in decreased blood flow and increased blood pressure. This invention may be used to arterialize blood vessels in the venous system to prepare them for an exposure to arterial pressures.

15 Claims, 5 Drawing Sheets

DEVICES, SYSTEMS AND METHODS FOR CONTROLLING LOCAL BLOOD PRESSURE

This application claims priority to U.S. Provisional Patent Application Ser. No. 60/630,563, filed Nov. 26, 2004, the content of which is hereby incorporated by reference in its entirety into this disclosure.

BACKGROUND OF THE INVENTION

1. Field of the Invention

The present invention relates to controlling blood pressure. More particularly, the present invention relates to devices, systems and methods for controlling blood pressure in vessels in vivo to change the physiology of such blood vessels.

2. Background of the Invention

An area of surgical medicine where the health and well-being of a patient have not progressed as well as the commonplace nature of the surgery is replacement of arteries due to damaged or diseased state. Although the option of introducing an artificial blood vessel has been used successfully for years, because of the inherent problems of biocompatibility and the resultant chance of implant rejection by the body as well as clotting and other factors, it is often most ideal to use a patient's own blood vessels when there is a need to substitute for a diseased or damaged vessel.

In such a procedure, when a patient's artery needs to be replaced with a substitute, a surgeon picks one of the patient's veins to serve as the substitute, thereby essentially avoiding any complications relating to biocompatibility. However, because the architecture of the veins tends to be significantly different than the artery that they were intended to replace, the transposed vein typically is exposed to conditions for which it is not designed, resulting in structural or physiological damage to the vein. One of the most significant factors that contribute to the failure of the vein in its new location is directly attributable to the significantly increased blood pressure inherent in the arterial system as opposed to the venous system.

Thus, a need exists in the art for an alternative to the conventional methods of replacing damaged or diseased arteries with veins from the same patient that allows the vein to better handle its new function and position but without the drawbacks of conventional methods, which include repeated care or operations or the inherent shock to the venous system from the shock of sudden exposure to arterial pressure.

SUMMARY OF THE INVENTION

The present invention provides an alternative and enhancement to conventional treatments for artery disease as well as other blood vessel conditions where the artery needs to be corrected through conventional methods, such as balloon catheter enlargement, or altogether replaced with another blood vessel, either artificial or natural. The present invention uses the findings that occluded blood vessels cause an increase in interior blood pressure, thereby allowing a thickening of the vessel wall, or "arterialization." Through use of unique devices, systems and methods, the present invention induces an arterialization of a desired section of the venous system through a gradual and minimally-shocking manner so that the venous system is conditioned to accept an increase in blood pressure, thereby making any eventual to increased blood pressure much less traumatic than conventional methods.

In exemplary embodiments, the present invention makes use of enclosures in blood vessels that enclose particles which increase in size, thereby resulting in an increased occlusion for the blood vessel, and resultant increase in pressure to the exposed blood vessels. This arterialization of the blood vessels conditions them for eventual increases in blood pressure so that they are better able to handle their new location when they are transposed to an arterial position within the body.

DETAILED DESCRIPTION OF THE INVENTION

The present invention provides systems and methods for addressing some of the problems associated with conventional methods of replacing arteries with veins. The problems that are common in such operations include the need for repeated operations, the relatively high level of further medical conditions or mortality resulting from the shock of the venous system to arterial pressure, and other drawbacks known to one having ordinary skill in the art.

Figure 1:
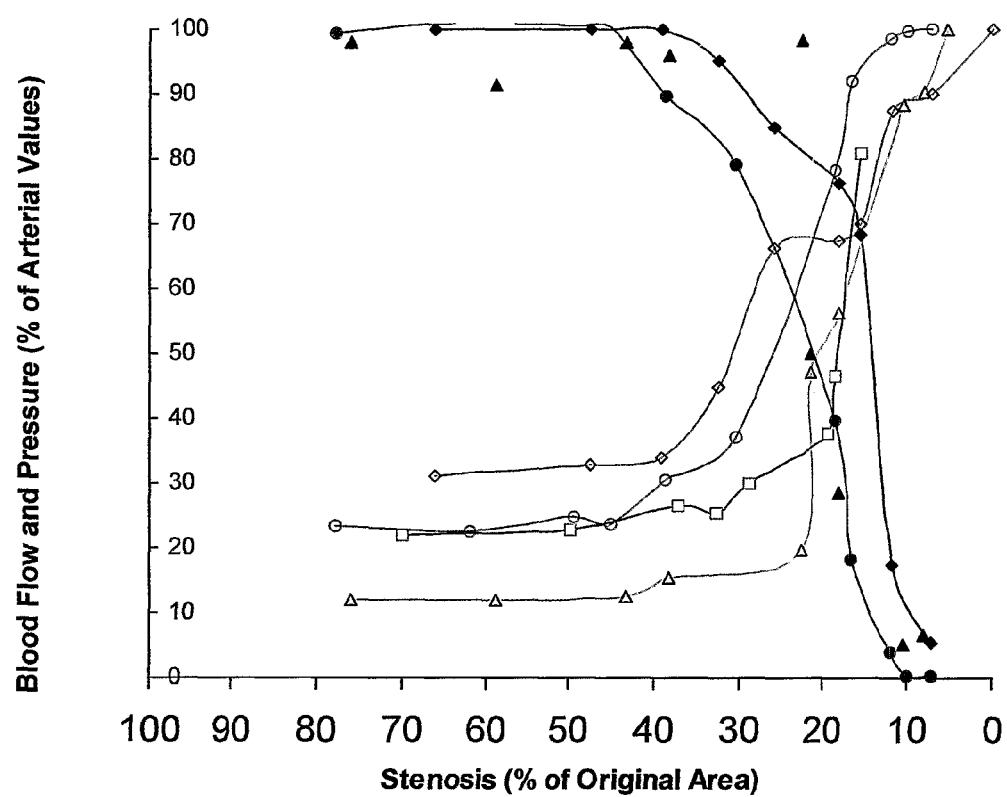
FIG. 1 shows a graph of the relation of blood flow (upper curves) and pressure (lower curves) with respect to changes in cross-sectional occlusion, as through a stenosis.

The present invention takes advantage of the findings of studies, shown in FIG. 1, that teach that blood flow remains mostly constant in a blood vessel as the cross sectional area decreases until a critical stenosis is reached. In other words, pressure increases steadily while the flow remains relatively constant until the critical stenosis point. Prior to about 80% stenosis, the increase in pressure is much more significant than the drop in blood flow. However, after the cross sectional area of an occluded blood vessel becomes about 20% of the original non-occluded cross-section of the vessel, internal blood pressure increases in a steady manner. As shown in FIG. 1, internal vessel pressure rises rapidly when the cross-sectional area of the blood vessel falls to 20% of original area and below. This may be explained by the natural distensibility and flexibility of the blood vessel to account for some natural occlusion. However, at about the threshold of 20%, the blood vessel loses its ability to account for any occlusion, and pressure increases rapidly while the blood flow decreases in an inversely similar manner. A conclusion that may be made is that patients who have blood vessels with some occlusion may not immediately sense the effects of such occlusion until the occlusion takes up some 80% of the cross-sectional area of a normal non-occluded blood vessel.

Studies have shown that blood vessels, particularly veins, have the ability to transform themselves into arterial-like vessels when an outside stimulus (for example, higher blood pressure) is imposed upon them. Using this finding, any attempt at transforming a vein into an arterial-like blood vessel through an increase in blood pressure brought about by vessel occlusion would necessarily require a stenosis that results in at least a 80% blockage of the natural cross-sectional area of the normal blood vessel. Stated differently, a stenosis would have to result in a cross-sectional area of about 20% of the original cross-sectional area of the blood vessel in order to begin to produce an increase in blood pressure that would result in the physiological changes necessary to transform a vein into an arterial-like vessel. Although the statements made here with respect to FIG. 1 refer to 80% occlusion and its corresponding cross-sectional area of 20%, such values are merely exemplary and dependent on the particular organ and sample being considered in FIG. 1. More representative values for specific organs or systems are dependent on those systems. The main teaching, however, is that pressure drops more rapidly than flow at a critical stenosis point as a blood vessel is increasingly occluded.

A rapid attempt at the transformation of a vein into an arterial-like vessel results in damage to the venous wall because of the shock of the step-like increase in blood pressure. In cases where a vein, with internal blood pressure in mmHg in the low teens to single digits is rapidly or in a step-like manner exposed to an arterial blood pressure, which is about an order of magnitude greater, the blood vessel attempts the process of physiological transformation to an arterial-like vessel quickly. However, the order of magnitude increase in pressure does not allow the architecture of the blood vessel to transform smoothly and in an orderly fashion, and deterioration of the blood vessel wall and other similar damage are not uncommon.

Part of the basis for the devices, systems and methods according to the present invention is to take advantage of the findings that blood vessels do have the ability to change from one form to another depending on the type of pressure to which they are exposed. However, the present invention also attempts to at least minimize if not eliminate the problems and drawbacks with conventional step- or rapid-exposure methods of exposing a vein to arterial pressure by creating a graded or gradual-increase in pressure to the vein.

Thus, systems and methods according to the present invention create an internal environment for the vein that results in a gradual increase and exposure to the levels of arterial blood pressure such that any risks of shock or disintegration of the blood vessel wall because of conventional exposure to a step-increase in blood pressure is minimized or avoided. Thus, various devices, systems and methods are introduced herein that have the ability to create a gradual increase in blood pressure within pre-determined areas of a blood vessel while maintaining relatively constant blood flow through the vessel. Although certain exemplary embodiments of the invention are shown, the invention is not limited to these mere examples, and has a scope beyond the examples shown herein, to all devices, systems and methods that have the capability of producing a graded increase in blood pressure within the interior of a blood vessel, resulting in a gradual transformation of blood vessel wall thickness from that of vein or venule to a more arterial-like vessel, so that such venous blood vessels are better prepared to handle the pressures of their new position on the arterial side after transplantation.

Figure 2:
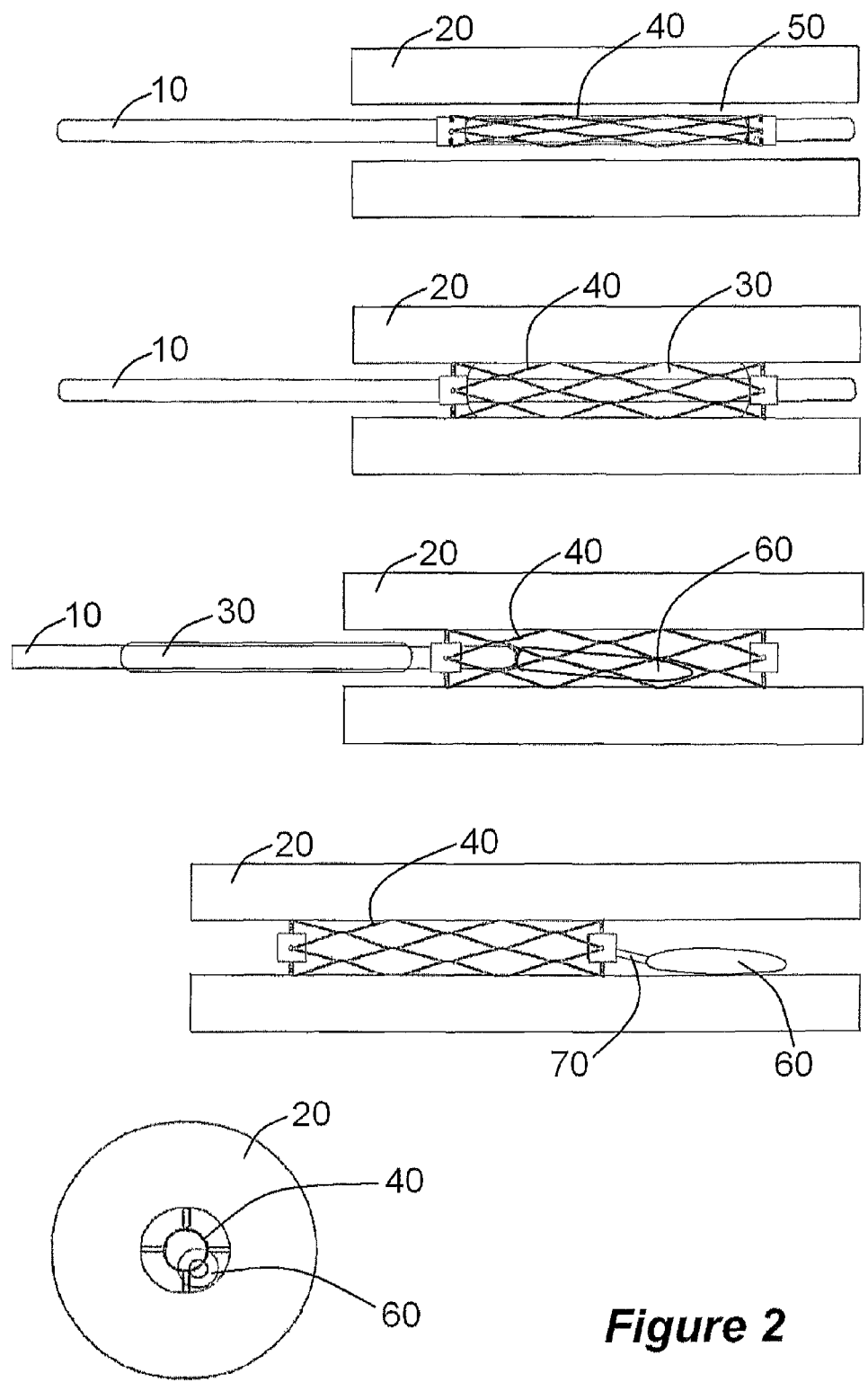
FIG. 2 shows an exemplary embodiment of the present invention as being introduced into a blood vessel through a conventional balloon catheter.

In an exemplary embodiment of the present invention, as shown in FIG. 2, a conventional balloon catheter 10 is used to enter a blood vessel 20. Such procedures are conventionally performed to increase the cross-sectional area of an at least partially occluded blood vessel, such as an artery. As used here, the same conventional method of inserting a balloon catheter inside a blood vessel is used to initially introduce the balloon catheter into a predetermined section of a desired blood vessel that needs to be conditioned for eventual transplantation to another part of a patient's body. Once in place, the balloon 30 is enlarged through conventional procedures. On the exterior of the balloon is a mesh-like enclosure that conforms to the contour of the balloon.

After the balloon is enlarged, the mesh-like enclosure (anchor or enclosure 40) is relatively anchored in place within the blood vessel (in lumen 50) by friction fit of its exterior points with the interior of the blood vessel wall. The balloon is typically then deflated and removed. However, the enclosure is then left in place, having been locked into place within the blood vessel.

Although such mesh-like enclosures may resemble conventional devices such as stents, the enclosure as described herein has a geometry that is distinguishable from conventional stents. As seen in the schematic cross sectional view in FIG. 2, the outer ends of the enclosure have an exterior wall that is used to create a cage-like environment within the interior space of the mesh-like enclosure. This cross-sectional view of the end walls is not drawn to scale but is enlarged to highlight its geometry. This architecture is unique and distinct from conventional stents, which typically attempt to maintain or enlarge the structural geometry of a portion of a blood vessel while, at the same time, not hindering blood flow therethrough by introducing anything that encroaches into the cross-sectional area of the blood vessel. In fact, the very purpose of many stents is to enlarge the blood vessel cross-sectional area, and not to impose upon it in any way.

As shown in FIG. 2 and described herein, and in contrast with conventional stents, the cage-like enclosure 40 that is created serves a purpose to act as a trap or guard to the movement of a particle 60, which is either trapped within the cage or is beyond the end walls of the cage or some combination thereof. Such geometry serves in the overall process of introducing a graded pressure increase environment, as described further herein.

Once the cage-like enclosure has been created, a particle may be introduced into its interior. This interior particle has a unique property of being expandable with increased exposure to the interior blood vessel environment. For example, it may be an object that retains fluids from the blood vessel when exposed thereto, or in response to a chemical introduced thereto.

In the exemplary embodiment shown in FIG. 2, the interior particle is a pill, made primarily of ameroid, a dehydrated protein structure. However, the present invention is not limited to pill shapes or ameroids or the combination. Any material of any shape may be used that is introducible to the blood vessel environment, does not create physiological harm, and is capable enlarging in time. Other shapes, such as masses (e.g., conventional children's play putty), or other materials, such as biocompatible polymers (e.g., hydrophilic polymers capable of attracting water) may also be used. One of ordinary skill in the art would be cognizant of other shapes and materials that may be used in the invention described herein, and all such other shapes and materials, although not described specifically herein for sake of brevity, are within the scope of the present invention.

As shown in the example of FIG. 2, an ameroid pill is introduced into the enclosure by the lumen of the catheter. The ameroid pill is initially dry as it is inserted into the enclosure. Once in the enclosure, the pill is exposed to the surrounding environment of the blood vessel, thereby gaining moisture and enlarging in reaction therewith. This gradual attraction of fluid and enlargement of the ameroid pill contributes to the gradual increase in girth and overall size of the ameroid pill. As blood continually flows through the blood vessel, as shown in FIG. 2, the ameroid pill enlarges within its confined area and continues to create a gradual decrease in cross-sectional area of the blood vessel. As shown in FIG. 1, once the cross-sectional area of a blood vessel is such that it is about 20% of the original area, then blood flow decreases somewhat while blood pressure increases noticeably, which results in physiological changes in the blood vessel walls which are exposed to this increase in blood pressure.

Use of the concept exemplified in FIG. 2 results in gradual conditioning of a blood vessel to increased levels of pressure such that its physiological changes in geometry are gradual, and not shockingly rapid. This will serve to decrease or prevent any of the conventional drawbacks of conventional methods where certain blood vessels, such as veins, are exposed to arterial blood pressures in a shocking step-like manner, resulting in high rates of eventual failure or vessel structure breakdowns.

In use, the concept shown in FIG. 2 may be used to assist in the improved conditioning of veins before they are introduced into locations where they serve as arteries. In the non-limiting example shown in FIG. 3, a device according to the present invention is introduced into a target vein, such as the femoral or saphenous vein, commonly used to replace diseased or damaged arteries in coronary artery bypass.

Figure 3:
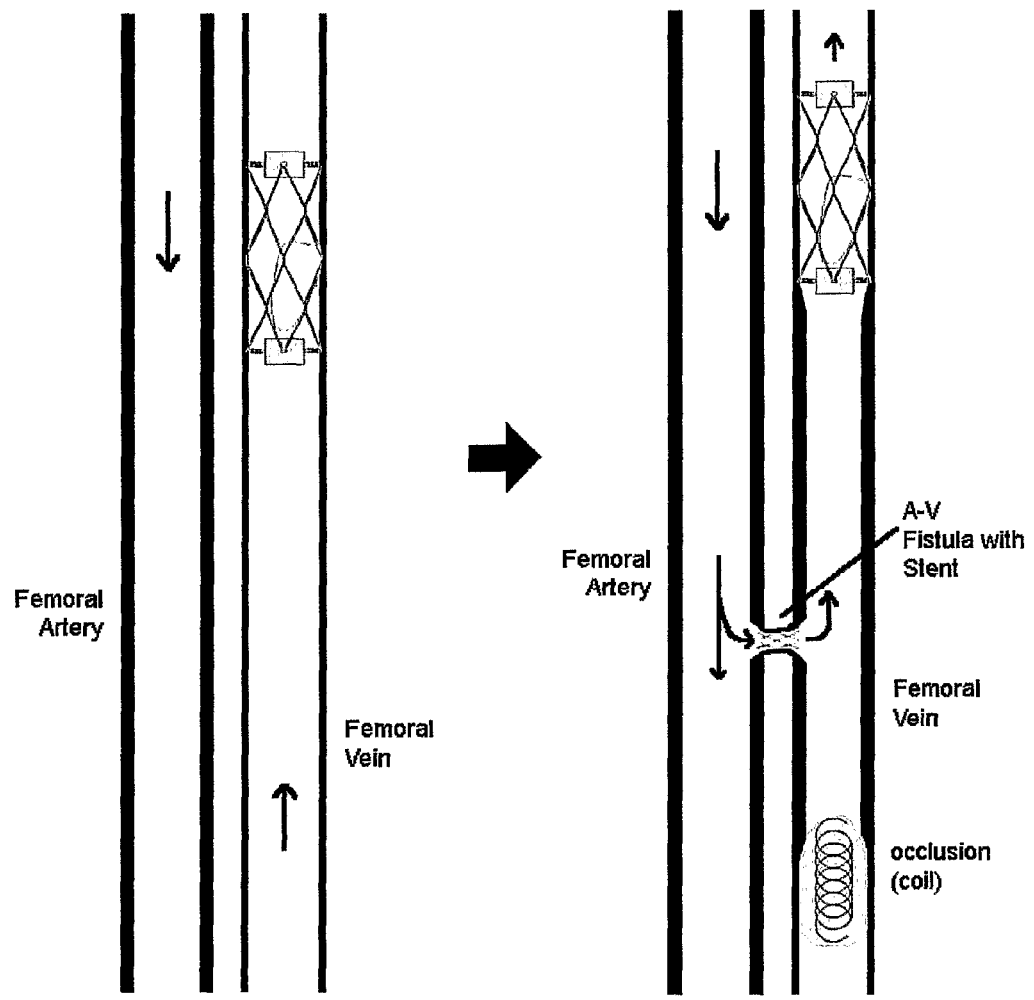
FIG. 3 shows a technique according to an exemplary embodiment of the present invention of arterializing a vein to prepare it for eventual relocation to an arterial position using an enclosure that serves to increase the pressure exposed on the interior of the vein.

As shown in the two exemplary steps of FIG. 3, a device according to the present invention is introduced into the interior of the femoral vein through conventional methods, such as the catheter method described with respect to FIG. 2. Once in place, the enclosure device allows exposure of the ameroid pill contained therein to the flow of blood traversing through the blood vessel. With time, the ameroid pill retains moisture from the flowing blood and increases in girth and size. As the ameroid pill increases in size, its overall volume serves to decrease the cross-sectional size of the blood vessel in which the enclosure is positioned. As shown in the graph of FIG. 1, with an increase in cross-sectional area occlusion, an increase in blood pressure occurs, particularly beyond a certain level of occlusion, as shown in FIG. 1. Thus, as the ameroid pill increases in size, the part of the femoral vein that is upstream of the enclosure increases in size as it arterializes in response to the increase in pressure.

At some point in time, the ameroid pill is enlarged to a point that it serves to significantly decrease, but not altogether stop, the blood flow through the femoral vein, as shown in the second diagram of FIG. 3. Although such decreased blood flow and near complete occlusion would create tissue hypoxia and eventual death if occurring on the arterial side, the highly vascular nature of the venous system allows for redundant flows to account for any such induced or natural vessel blockage. Furthermore, the time required to create such blockage is determinable by a health care professional as a function of the size of the blood vessel area being blocked as well as the size of the ameroid pill and the absorbency qualities of such a pill. Such factors would be known to one having ordinary skill in the art without the need for undue experimentation. For example, in pig studies, it has been found that a two week period is sufficient for arteralization of veins.

Further, the shape of the ameroid may be any that functions according to the description presented herein. A particular embodiment of the ameroid pill, as shown in exemplary embodiments, is in the configuration of a bullet, with transitionally tapered ends, thus enabling less hemodynamic flow disturbances and greater streamlined flow.

When it has been determined that the time of exposure of the femoral vein to a low-flow condition has been sufficient to initially arterialize the blood vessel in a healthy manner, a surgeon can then introduce an induced occlusion in an upstream location with respect to the implanted enclosure, as shown in the second diagram of FIG. 3. Furthermore, an A-V fistula with a stent is created in position on the femoral vein somewhere between the induced occlusion upstream thereto, and the enclosure with particle downstream thereto, such that femoral artery blood flows into the femoral vein and is directed through the reduced flow enclosure located downstream. The femoral vein, having been exposed to a reduced flow (and increased pressure) environment for a time period that allowed it to arterialize by thickening its walls, is now not as "shocked" by its sudden exposure to femoral artery pressure through the fistula.

Thus, at the least, the femoral vein would be exposed to one much smaller step increase in pressure using the teachings of the present invention, as opposed to one very large increase in blood pressure exposure. In essence, blood vessels that have undergone the methods taught by the present invention are exposed to a gradual increase in pressure to a given high point for the femoral vein, at which time, they are then introduced to a higher pressure level (when A-V fistula created), where the higher pressure level is not as high a step increase as it would be using conventional surgical methods.

As determined by a surgeon, the time exposure of a patient to the condition shown in the second diagram of FIG. 3 would be dependent on various factors, including the level of further arterialization needed, the type of particle being used, as well as other factors known to one having ordinary skill in the art. When the desired time is reached, the surgeon can then safely close off the fistula as well as positions at the upstream induced occlusion sight and the downstream enclosure sight, and remove the portion of the femoral vein positioned therebetween, which has been exposed to higher blood pressures from the femoral artery and conditioned to better accept its position in the arterial side of the circulatory system. The thickened wall portion of the femoral vein is then transplanted into its new pre-designated higher pressure location for which it has been conditioned to withstand. This decreases any eventual shock that the femoral vein would have been exposed to had it not been pre-conditioned for the additional pressure.

Although the examples above have shown the ameroid pill (a particle 60) being located inside of the cage-like enclosure, the present invention is not limited to such an architecture, nor are other alternatives not possible. For example, the ameroid pill may be positioned outside of the cage-like enclosure and attached thereto through an attaching medium 70 such that the increased size and girth of the pill serves to decrease the flow of blood past the enclosure.

Figure 4:
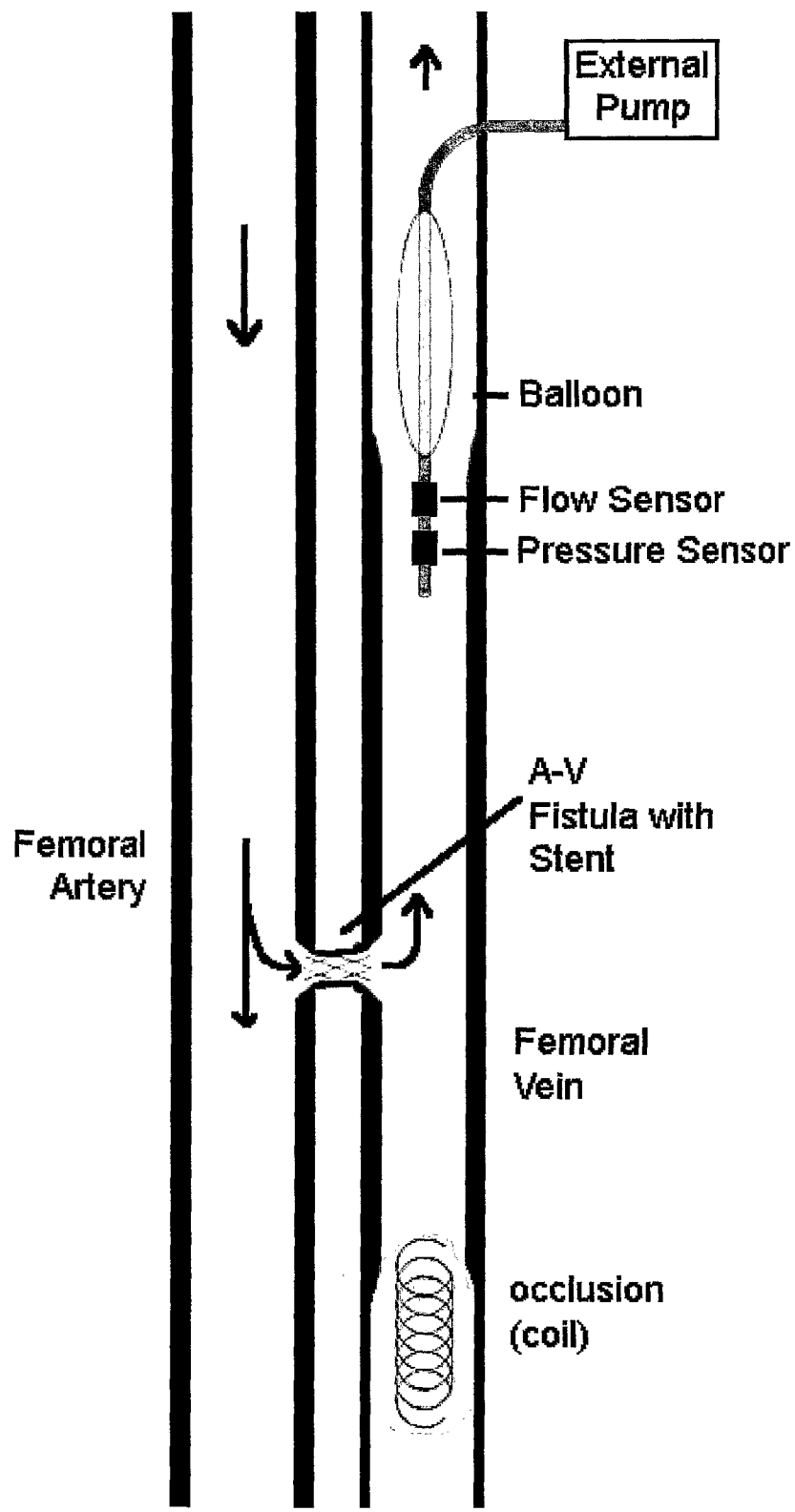
FIG. 4 shows a technique according to an exemplary embodiment of the present invention of arterializing a vein to prepare it for eventual relocation to an arterial position using an externally-controlled intravascular balloon that serves to increase the pressure exposed on the interior of the vein.
Figure 5:
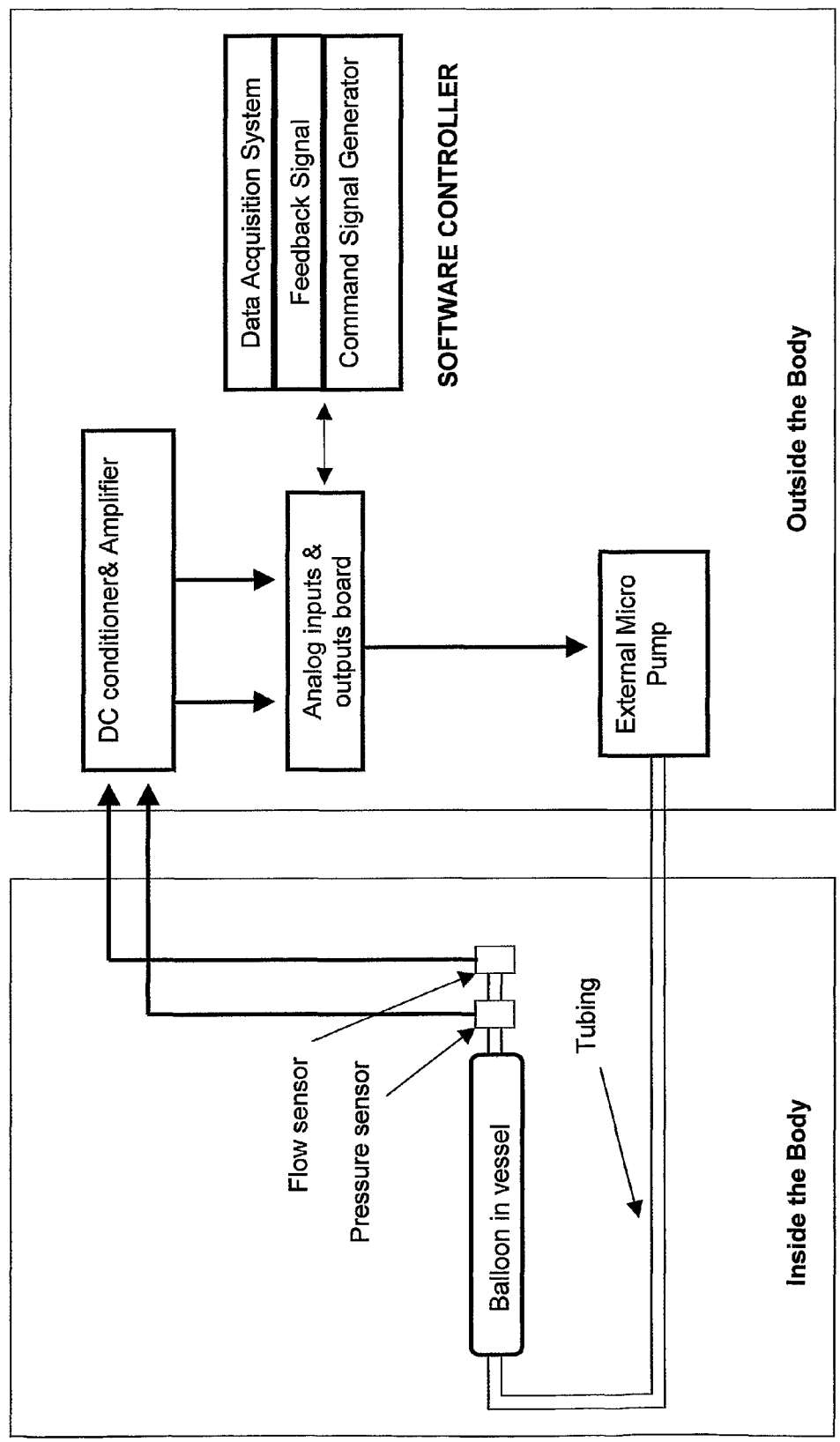
FIG. 5 shows a schematic diagram of a system according to the present invention and shown in FIG. 4 having internal and external components working in unison to control the intravascular pressure within a blood vessel.

In another exemplary embodiment of the present invention shown in FIGS. 4 and 5, an alternative approach is taken in arterializing a vein which introduces a balloon catheter into the a-v fistula. In this exemplary embodiment, the ameroid pill and surrounding cage is replaced by a more controlled system. A balloon is introduced into the femoral vein, in a similar geometry as that shown with respect to FIG. 3. However, as shown in FIG. 4, the balloon is positioned on tubing that has sensors positioned in a more distal position thereon. Such sensors could include, for example, a flow sensor and a pressure sensor. Other sensors are also possible and apparent to one having ordinary skill in the art.

Proximal to the balloon is tubing that leads to outside of the body and into an externally located micro pump. This pump is used to control the size of the balloon which is positioned inside of the femoral vein. In use, the pressure and flow are continuously sensed and the balloon volume is adjusted to increase the pressure at the desired rate. Control and feedback circuitry is needed to allow for proper inflation of the balloon. Such control mechanism includes, for example, DC conditions and amplifier, analog input and output board, and a software controller, which includes a data acquisition system, a feedback signal sensor, and a command signal generator.

In use, the sensors (e.g., flow, pressure) located within the intravascular space, send signals to the DC condition and amplifier through hard wire and/or wireless transmission, wherein such signals are then forwarded to the analog input/outboard. There it is in communication with the software controller, which then, depending on the measured flow and/or pressure, transmits a command back to the output board which then directs a change in the external pump, directly affecting the size of the balloon inside of the vascular space.

This dynamic controller system, shown in FIGS. 4 and 5, allows for feedback control of the rate of pressure change. For example, if the internal blood pressure is too low, the feedback system loop allows for an inflation of the balloon resulting in increased blood pressure. Alternatively, if the blood pressure is too high, the feedback loop allows for a deflation of the balloon resulting in decreased blood pressure. Although the sensors, balloon, and other individual components used in the present embodiments may be apparent to one having ordinary skill in the art, the system as a whole and the manner of use resulting in a feedback controlled blood pressure controller, is novel and non-obvious and presents a significant advantage over other conventional techniques in use today. Further, the position of the sensors may be interchanged as needed without departing from the invention.

As shown in the block diagram of the set-up in FIG. 5, the external portion of the system may be placed in a small jacket strapped to the leg of the patient for the period (e.g., two weeks) of the arterialization. Other positions and configurations are also possible and within the scope of the present invention. After a vein is arterialized using the technique shown here, the patient is ready for surgery. At the time of surgery, the arterialized vein would be harvested and the balloon catheter removed.

The foregoing disclosure of the preferred embodiments of the present invention has been presented for purposes of illustration and description. It is not intended to be exhaustive or to limit the invention to the precise forms disclosed. Many variations and modifications of the embodiments described herein will be apparent to one of ordinary skill in the art in light of the above disclosure. For example, the principles described above may be applied to pre-condition other vessels in the venous systems other than that described for the femoral vein. The scope of the invention is to be defined only by the claims appended hereto, and by their equivalents.

Further, in describing representative embodiments of the present invention, the specification may have presented the method and/or process of the present invention as a particular sequence of steps. However, to the extent that the method or process does not rely on the particular order of steps set forth herein, the method or process should not be limited to the particular sequence of steps described. As one of ordinary skill in the art would appreciate, other sequences of steps may be possible. Therefore, the particular order of the steps set forth in the specification should not be construed as limitations on the claims. In addition, the claims directed to the method and/or process of the present invention should not be limited to the performance of their steps in the order written, and one skilled in the art can readily appreciate that the sequences may be varied and still remain within the spirit and scope of the present invention.

What is claimed is:

1. A device for exposing a blood vessel to increased pressure, the device comprising:
    an anchor that locks into and spans across a cross-sectional area of a lumen of a blood vessel, the anchor configured to be positioned at one end of and around an outer circumference of a balloon catheter used to deliver the anchor and further configured for expansion by way of inflating a balloon coupled to the balloon catheter;
    a particle that is prevented by the anchor from flowing away in a direction of blood flow in the lumen of the blood vessel;
    wherein the particle enlarges gradually with exposure to blood flow, thereby decreasing the cross-sectional area of the lumen that is exposed to blood flow, resulting in a decrease in blood flow; and
    wherein the anchor expands independently of the particle.

2. The device of claim 1, wherein the particle is an ameroid particle.

3. The device of claim 1, wherein the particle is trapped within the anchor.

4. The device of claim 1, wherein the particle is coupled to but disposed outside of the anchor.

5. The device of claim 1, wherein the particle is initially dry at a time of introduction into the lumen of the blood vessel.

6. A system for exposing a blood vessel to increased pressure, the system comprising:
    an elongated catheter having a balloon coupled thereto;
    an enclosure at one end of the catheter and positioned around an outer circumference of the catheter that locks into and spans across a cross-sectional area of a lumen of a blood vessel due to expansion of the balloon;
    a particle that is prevented by the enclosure from flowing away in a direction of blood flow in the lumen of the blood vessel;
    wherein the elongated catheter is configured to deliver the enclosure and the particle into the lumen of the blood vessel;
    wherein the enclosure expands independently of the particle; and
    wherein the particle enlarges gradually with exposure to blood flow, thereby decreasing the cross-sectional area of the lumen that is exposed to blood flow, resulting in a decrease in blood flow.

7. The system of claim 6, wherein the particle is an ameroid particle.

8. The system of claim 6, wherein the particle is trapped within the enclosure.

9. The system of claim 6, wherein the particle is coupled to but disposed outside of the enclosure.

10. The system of claim 6, wherein the particle is initially dry at a time of introduction into the lumen of the blood vessel.

11. A method for exposing a blood pressure to increased pressure, the method comprising:
    introducing an anchor into a lumen of a blood vessel using a catheter, the anchor positioned at one end of and around an outer circumference of the catheter;
    expanding the anchor by inflating a balloon coupled to the catheter to lock the anchor and place within the lumen of the blood vessel; and
    introducing a particle in communication with the anchor using the catheter and after the step of expanding the anchor, wherein the particle increases in volume with increased exposure to fluid in the lumen of the blood vessel;

wherein the anchor expands independently of the particle; and wherein the particle decreases a cross-sectional area of the lumen as it grows in volume, resulting in decreased blood flow in the blood vessel.

12. The method of claim 11, wherein the particle is an ameroid particle.

13. The method of claim 11, wherein the particle is trapped within the anchor.

14. The method of claim 11, wherein the particle is coupled to but disposed outside of the anchor.

15. The method of claim 11, wherein the step of introducing the particle is performed by introducing the particle that is initially dry at a time of introduction into the lumen of the blood vessel.

* * * * *